United States Patent [19]

Goodfellow et al.

[11] Patent Number: 5,314,482
[45] Date of Patent: May 24, 1994

[54] FEMORAL COMPONENT, TOOL AND METHOD

[75] Inventors: John W. Goodfellow, Woodeaten; John J. O'Connor, Headington, both of England

[73] Assignee: British Technology Group Ltd, London, England

[21] Appl. No.: 789,772

[22] Filed: Nov. 8, 1991

Related U.S. Application Data

[63] Continuation of Ser. No. 306,075, Feb. 6, 1989, abandoned.

[30] Foreign Application Priority Data

Feb. 5, 1988 [GB] United Kingdom ............... 8802671

[51] Int. Cl.⁵ ............................................. A61F 2/38
[52] U.S. Cl. .................................... 623/20; 606/88
[58] Field of Search ....................... 623/16, 18, 20; 606/86-88

[56] References Cited

U.S. PATENT DOCUMENTS

| | | |
|---|---|---|
| 3,852,830 | 12/1974 | Marmor . |
| 3,958,278 | 5/1976 | Lee et al. .............................. 623/20 |
| 4,085,466 | 4/1978 | Goodfellow et al. .............. 623/20 |
| 4,246,895 | 1/1981 | Rehder ............................ 128/92 VV |
| 4,355,429 | 10/1982 | Mittelmeier et al. ............... 623/20 |
| 4,474,177 | 10/1984 | Whiteside ..................... 128/92 VW |
| 4,634,444 | 1/1987 | Noiles . |
| 4,719,908 | 1/1988 | Averilli et al. ....................... 623/20 |
| 4,838,891 | 6/1989 | Branemark et al. ............... 623/20 |

FOREIGN PATENT DOCUMENTS

| | | |
|---|---|---|
| 2748452 | 5/1979 | Fed. Rep. of Germany ... 128/92 JJ |
| WO8503425 | 9/1985 | PCT Int'l Appl. . |
| 0577020 | 10/1977 | U.S.S.R. ........................ 128/92 VW |
| 1383474 | 2/1975 | United Kingdom . |
| 1395896 | 5/1975 | United Kingdom . |
| 1485681 | 9/1977 | United Kingdom . |
| 1534263 | 11/1978 | United Kingdom . |
| 2215610A | 2/1989 | United Kingdom . |
| 2245175A | 1/1991 | United Kingdom . |
| 2247407A | 9/1991 | United Kingdom . |

OTHER PUBLICATIONS

"Broomhead's Improved Reamers", Journal of Bone and Joint Surgery, p. xii, No. 1951.
"Eftekhar II Knee Prosthesis", a publication by Zimmer, Warsaw, Indiana; 14 pages, 1982.

*Primary Examiner*—David Isabella
*Attorney, Agent, or Firm*—Cushman, Darby & Cushman

[57] ABSTRACT

A prosthetic femoral component (40) for the knee joint has a body (41,42) defined between elongate articulation and securement surfaces (43; 44,45), the articulation surface (43) being convexly spherically shaped and the securement surface having major and minor areas at opposite end portions, the major area (44) being essentially concavely spherically concentric with the articulation surface to form a shell body part (41), and the minor area (45) being essentially planar extending chordally of the articulation surface. A bone-penetrating pin (46) preferably extends radially from the major securement surface area in a direction parallel to the longitudinal direction of the neighbouring minor area. A related surgical tool (50) for shaping the femoral condyle has a rotary cutter (52) to provide a cut bone surface complementing the component major area, and a guide spigot (53) projecting adjustably coaxially within the cutter.

10 Claims, 2 Drawing Sheets

PRIOR ART

FEMORAL COMPONENT, TOOL AND METHOD

This is a continuation of application No. 07/306,075, filed on Feb. 6, 1989, now abandoned.

BACKGROUND OF THE INVENTION

This invention concerns orthopaedic joint components, tools and methods more particularly for use in relation to the femur at the knee joint. The invention has in fact been conceived initially with a view to application as or for a femoral component of so-called unicompartmental form in a prosthesis according to U.S. Pat. No. 4,085,466. It is accordingly appropriate to describe the invention in more detail in terms of such application, but it is to be understood that the invention is more widely applicable to other forms of prosthesis.

In the present context "unicompartmental" qualifies a component discretely applicable to a femoral condyle to provide a replacement articular surface. While two such components can be used on the associated condyles of a joint, this distinguishes from a bicompartmental component in which a single one-piece femoral component has an associated pair of condylar parts connected by a bridging portion, and also from a tricompartmental component in which the bridging portion defines a patellar articular surface.

In the same context "surface replacement", used hereinafter, involves the provision of a component having a body largely of shell form and defining two principal surfaces in back-to-back disposition, one such surface being intended as the replacement articular surface and the other such major surface to interface with the relevant bone. In this case the bone is of course the femur at the knee and the respective principal surfaces are commonly grossly convex and concave.

Unicompartmental components presently in routine use include two principal types. In each type the articular surface is normally of polyradial shape, that is to say the surface is deliberately non-spherical. This shaping appears to reflect confused thinking which assumes a need for a varying center of curvature for the articular surface in direct relationship with the fact that there is in the natural situation, a varying center of rotation between the femur and tibia during flexion-extension movement. Generation of the latter variation is of course appropriate following surgery if the natural joint function, including the action of retained ligaments, is itself to be closely simulated but study in development of the present invention finds no necessity for a related polyradial curvature.

The routinely used types differ, however, in the form of interface surface configuration used in relation to securement of the component to the bone. In one type the interface surface consists of a plurality of plane facets intended for securement, with or without bone cement, against a closely matched surface cut on the condyle. The other type is of surface replacement form and the corresponding interface surface closely follows the polyradial shape of the articular surface. This type is intended for securement with cement, the condyle being at best relatively coarsely prepared in terms of matching and the cement being deployed to fill gaps resulting from mismatching.

There are difficulties and disadvantages with both types. For the one type the related bone preparation is complex by virtue of the need to cut plural facets in a predetermined relationship to match the component. Moreover this difficulty is compounded by the repetition which is necessary if the bone shaping requires relocation to attain a better final position for the component. Also the interface between the component and bone will necessarily be irregular relative to the trabecular structure of the latter and this will result in the transmission of non-compressive forces through the interface during subsequent patient use of the joint, which forces can lead to component loosening. For the other type the final position for the component is determined in an effectively arbitrary manner and this cannot be reliably compatible with maintenance of normal ligament action or, therefore, joint function.

SUMMARY OF THE INVENTION

An object of the present invention is to reduce these difficulties and disadvantages.

To this end the invention in one aspect provides a prosthetic femoral component for the knee joint comprising a body defined between two principal surfaces in back-to-back disposition, one of such surfaces being of three-dimensionally curved convex shape to serve a condylar articular function, the other such surface being grossly concave and having at least a major area thereof shaped essentially as a surface of revolution to form with the corresponding area of the one surface a shell, and the component being adapted to engage the femur by way of said other surface with the axis of rotation of said area parallel to the longitudinal axis of the femoral shaft.

This component is preferably of unicompartmental surface replacement form.

Preferably the one principal surface and/or major area of the other principal surface is/are spherically shaped and when both are so shaped they are preferably concentric.

The remainder of said other surface from said area is conveniently a plane facet.

In another aspect the invention provides, for use with a component according to the invention, a surgical tool for shaping a femoral condyle, the tool having concave cutting means rotatable about an axis therethrough to describe a surface of revolution substantially equating with that of said component major area, and having a guide member projecting coaxially within said cutting surface.

Preferably in such a tool the cutting means and guide member are relatively adjustable to vary the effective axial length of the latter within the former.

In a further aspect the invention provides, for a component according to the invention, a method of preparing a femoral condyle which comprises exposing that condyle, locating the condyle in a position of flexion with its posterior portion immediately adjacent the tibia, forming a bore in the inferior portion of the condyle which bore is axially parallel to the longitudinal axis of the femur and located radially at a predetermined spacing from the tibia in said position of flexion, and shaping the condyle to form the same substantially to the complement of said surface of revolution this, complementary shaping being located coaxially with said bore, and to a predetermined spacing from the tibia in a position of full extension.

Preferably the predetermined spacings of this method are substantially equal.

BRIEF DESCRIPTION OF THE DRAWINGS

These aspects of the invention together with the preferred and other forms thereof will be clarified by consideration of the following further description given by way of example with reference to the accompanying drawings, in which.

DETAILED DESCRIPTION OF THE PRESENTLY PREFERRED EXEMPLARY EMBODIMENT

Figure 1:
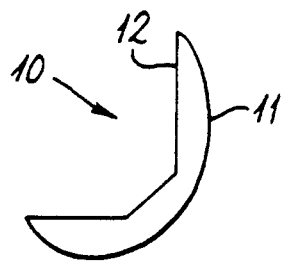
FIGS. 1 and 2 respectively schematically illustrate two types of prior art unicompartmental femoral component.

FIG. 1 schematically illustrates in side view a unicompartment femoral component 10 of the first type referred to above. The component has a main body of elongate form as shown defining an articular surface 11 and an interface surface 12. The articular surface 11 is longitudinally curved in polyradial manner with progressive increase in curvature towards one end, which end is to be sited posteriorly, and the surface is also transversely curved. The interface surface 12 consists of three plane facets but will commonly be supplemented with one or more projecting elements, usually of pin and/or blade form, to penetrate the bone for purposes of securement.

Figure 2:
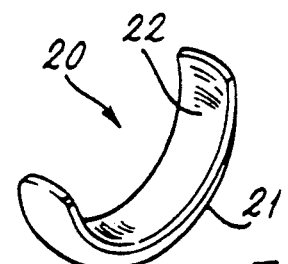

FIG. 2 schematically illustrates in a perspective view a unicompartmental femoral component 20 of the second type referred to above. This component is of surface replacement form and has a shell body of elongate form as shown defining a polyradial articular surface 21 similar to surface 11 in FIG. 1 and an interface surface 22 which closely concavely approximates surface 21. Again the interface surface 22 will commonly be supplemented by one or more elements to aid securement with bone, but this will usually be in a less pronounced manner to form a key with cement.

Figure 3:
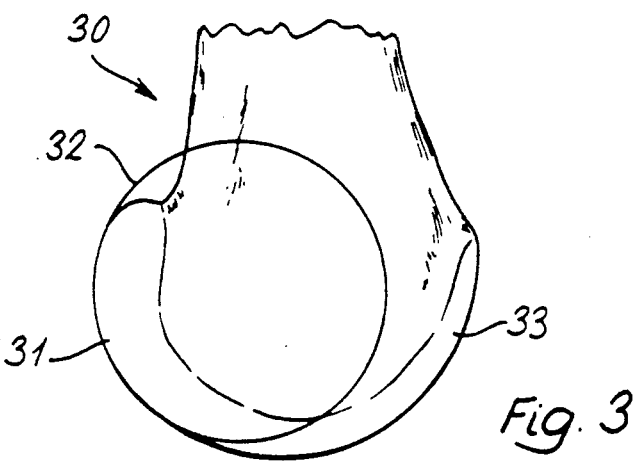
FIG. 3 illustrates natural shaping in the femur at the knee joint, FIG. 4 diagrammatically illustrates in side and plan views (a) and (b) one embodiment of a component according to the invention, FIG. 5 similarly illustrates a related surgical tool for use in application of the component of FIG. 4.

FIG. 3 illustrates natural shaping in the femur 30 at the knee joint by way of a diagrammatic section through the sulcus of the trochlear groove. The longitudinal, that is to say the anters-posterior profile of the condyle is seen at 31. Development of the invention rests, in part, on the consideration that this profile and also the related transversely extending areas of the condyle can be very closely represented by a spherical surface as indicated by the circular outline 32. Moreover such a sphere is found to be of substantially constant radius over large bodies of adult population. This consideration is, of course, counter to current thinking and femoral component design and indicates that only a small range of sizes for a component according to the invention will be needed.

Also, although condylar surface appears to be continuous with that of the trochlear groove in which the patella articulates, the areas of these surfaces which in fact perform a significant articular function in respective relation to the tibia and patella are found to be quite separate. The trochlear groove area in question is indicated at 33. This again contradicts current thinking whereby femoral components commonly exhibit features designed to accommodate patellar articulation even when the component is not of tricompartmental form.

These considerations and findings in development of the present invention led to the view that an idealised femoral component can have spherical articular shaping. The component is preferably unicompartmental to give flexibility for use in relation to different joint conditions without entailing a necessary constraint to accommodate patella function in all conditions. The component is preferably of surface replacement form with an interface surface which is spherical and concentric with the articular surface. This will simplify manufacture of the component, minimise the need for bone removal and, because the interface will be positioned in a substantially regular manner perpendicularly across the adjacent trabecullar structure, minimise the transmission of non-compressive forces to the bone.

Figure 4A:
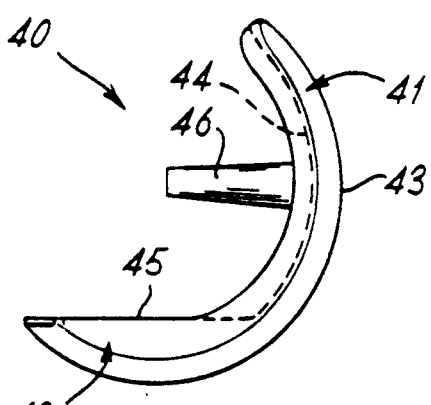
Figure 4B:
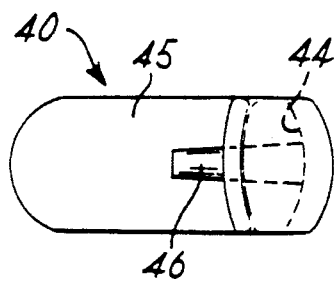

Practical development of the invention to date closely approaches this ideal by way of the unicompartmental component 40 of FIG. 4. This component is of one-piece construction and elongate form having a main body composed of a shell body portion 41 for application to the inferior part of a condyle and a continuing secondary body portion 42 for application to the posterior part of the condyle. The component defines a convex spherical articular surface 43 extending continuously over both body portions, while the shell portion defines a major interface surface area 44 substantially of concave spherical shape concentric with articular surface 43, and the secondary portion defines a minor interface surface area 45 of substantially planar shape extending chordally relative to surface 43. The component additionally has a pin 46 projecting radially inwardly from surface 44 and with its axis in parallel and symmetrical relation with surface 45.

The component of FIG. 4 differs from the above ideal for compatability with the practical development to date of related securement techniques.

Figure 5:
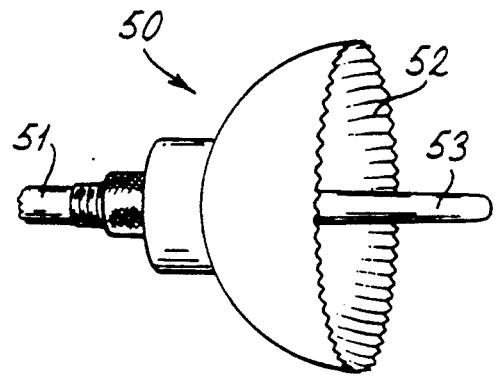

These techniques involve a cutting tool 50 of the form shown by FIG. 5. The tool can be termed a spigotted spherically-concave end mill. The tool has a shaft 51 for operable engagement at its free end in a suitable rotary power source. At its other end the shaft carries the milling cutter 52, the concave spherical cutting face of which is coaxial with the shaft and shaped to equate with the interface surface area 44 of the associated component. A spigot 53 projects radially inwardly of the cutting surface coaxially from the shaft, the relative positions of the cutter and spigot being adjustable axially of the latter in a continuous or discrete incremental manner by a screw or other mechanism. This adjustment suitably covers a small range of movement about a datum length for the spigot equal to the articular spherical radius of the related component.

Successive stages of the presently developed technique are illustrated by the remaining drawings.

In this technique the knee joint is suitably exposed, and a plane facet cut on the tibial plateau of the relevant compartment. This facet is to serve as a basis for securement of a tibial component for association with the subject femoral component, these components being additionally associated with a meniscal component therebetween if the teaching of U.S. Pat. No. 4,085,466 is followed.

Figures 6A, 6B:
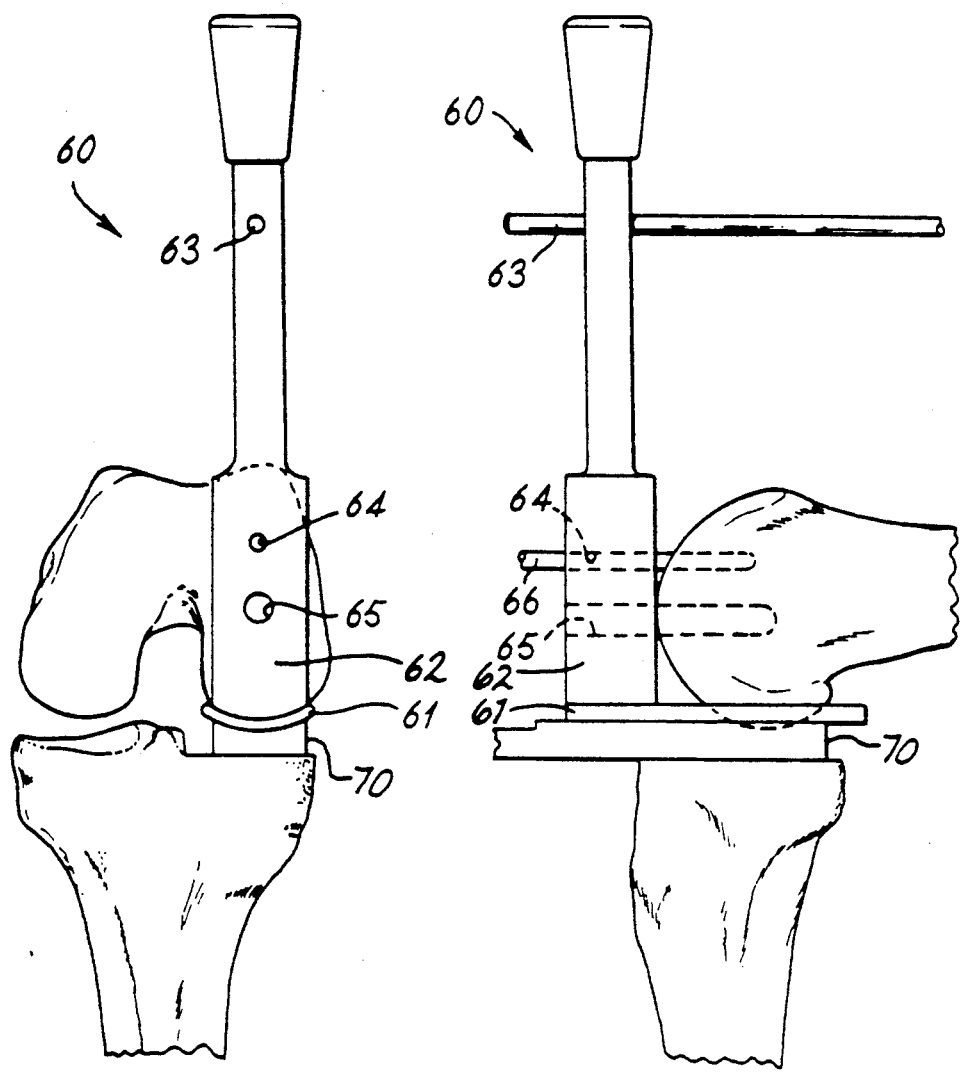
FIGS. 6a and 6b illustrates front and side view of the surgical tool as attached to the knee joint FIGS. 7 and 8 schematically illustrate successive stages in a procedure for application of the component of FIG. 4.

With the joint in a position of about 90° flexion as shown respectively in front and side views (a) and (b); in FIG. 6, a jig 60 of basically three-part form is applied to locate a shoe part 61 between the plane facet already cut and the now-facing posterior portion of the related femoral condyle, a drill guide part 62 across the inferior portion of the condyle, and an alignment part 63 extending parallel to the longitudinal axis of the femoral shaft. The shoe part 61 has an elongate face which is concavely transversely curved against the condyle. The guide part 62 has a smaller bore 64 and a larger bore 65, each axially parallel with the alignment part 63 and in a common plane with the latter. The alignment part 63 is shown to extend externally of the femur, but in an alternative form it can extend internally of the bone in the medullary canal.

The jig 60 is positioned as indicated in association with a spacer 70 between the shoe part 61 and the tibial plane facet, this spacer serving to represent the thickness of the associated tibial component to be secured to such facet, plus the thickness of any related meniscal component. More specifically this location is such as to position the guide part bore 65 substantially in alignment with the normal spherical radius at the neighbouring point of the condle and at a spacing above the spacer 70 corresponding to the radius R of sphericity for the articular surface 43 of the component intended for use. The radius R is, of course, determined on the basis of preceding X-ray or other presurgical examination, and/or assessment following exposure of the joint, substantially to match that of the condyle to be resurfaced.

This jig positioning will result in ligament action being sustained in a normal manner at flexion. Also, it is to be noted that such positioning is determined, in part, by reference to the posterior portion of the condyle where damage due to arthrosis occurs late in the progression of the condition to be obviated by prosthesis. Thus component positioning is determined by reference to joint geometry which is commonly viable in indicating normality for the patient.

In any event, when so positioned, the condyle is drilled by way of guide part bore 64 and a pin 66 engaged to stabilise the jig position. Then, the condyle is drilled through guide part bore 65 to a depth R.

Figures 7, 8:
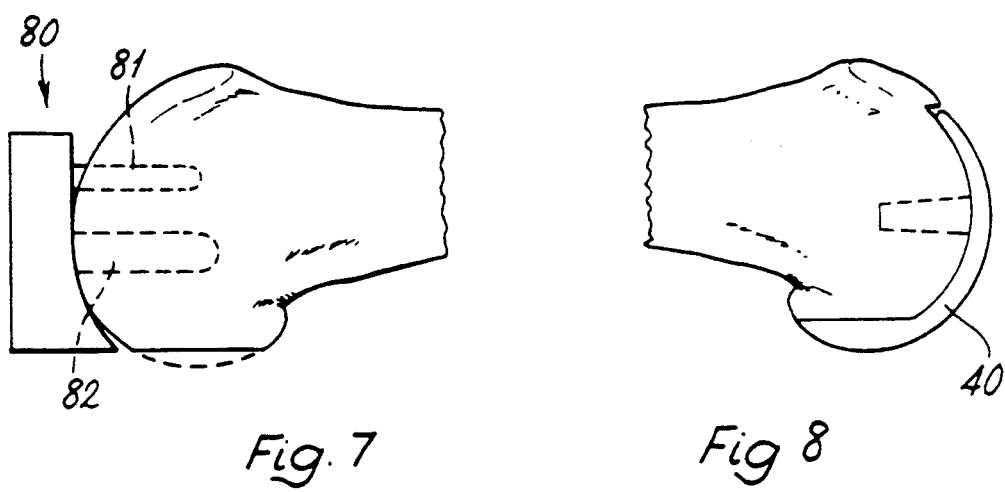

The next stage following use of jig 60 involves application of a saw block 80 to the condyle whereby the posterior portion can be removed to leave a plane facet as shown by FIG. 7. This saw block has pins 81 and 82 to engage in the condyle bores and so position the block in a stable manner.

Thereafter the tool 50 is applied to engage its spigot in the second formed bore in the condyle. Operation of the tool cuts the inferior portion of the condyle to leave a spherically convex face, this face being of markedly higher quality than that from a saw or other tool.

It is to be noted that the tool 50 is operated with its spigot limiting the depth of cut into the bone and that adjustment can be made to progressively reduce the spigot length while allowing intervening applications of the component, or a trial form thereof, to test the positioning by reference to ligament action with the joint extended.

Initially, the spigot length will be R with successive small reductions, of about 0.5 mm, say, being made to this length until testing shows that the component will be equally spaced from the tibia at about 90° flexion and full extension by the thickness of the associated tibial component pl us any related meniscal component. It will be appreciated that this progressive adjustment towards the desired result is simplified by the fact that the condyle has previously been sawn to provide a plane facet extending parallel to the direction of adjustment whereby the overall cut area of the condyle does not change in shape at any stage during use of the tool 50. Prismatic or other facetted shapes extending parallel to the direction of adjustment will give a similar facility.

The resultant shaping of the condyle will be seen to receive the component of FIG. 4 as shown in FIG. 8.

A remaining point to note in relation to the component of FIG. 4 is that the interface surfaces 44 and 45 will conform very closely to the indicated spherical and planar shapings, but in practice can vary in fine detail for the purposes of securement. For example, if securement is to rely on the use of cement, these surfaces may be formed with a roughened finish to afford a key while having the indicated overall shapes. Alternatively, or in addition, these surfaces can be relieved to a small extent to provide the same overall shaping within a low peripheral rim whereby a uniformly thin layer of cement is provided between the component and bone during securement. Similarly, where securement involving bone growth is intended, the related component surfaces can be formed with fine pores or like irregularities in accordance with established techniques, while still exhibiting the indicated overall shaping. In this case, the component surfaces can, for example, be relieved such as just mentioned and filled back to the desired shapes with hydroxyapatite or other suitable material.

While the invention has been more fully described with reference to the drawings, it has been indicated in the preceding description that wider application is possible.

Other unicompartmental forms can be advantageous relative to present routine components. For example a polyradial rather than spherical articular surface can be used while employing interface surfaces as described to obtain the related benefits of the latter. Conversely, or in addition, the spherically shaped interface surface area can be of non-spherical revolutionary shape while still allowing benefit from a simplified securement procedure. Again the illustrated form may be improved to have a wholly spherical or other rotationally defined interface surface for use in association with further developed securement procedures.

To the extent that the impact of the invention is wholly confined to treatment of the femoral condyle, the invention is of course applicable to bi- and tricompartmental forms of component.

Similarly the invention, while conceived in relation to use in prosthetic devices involving tripartite femoral, tibial and intervening meniscal components, the invention is equally applicable to device forms involving directly engageable femoral and tibial components.

We claim:

1. A method of preparing a femoral condyle for securement thereto of a prosthetic component having a bone engaging concave surface configured for fixation to the bone of said condyle, said surface having at least a major area shaped as a concave segment curved in each of three-dimensions thereby substantially defining a surface of revolution about an axis therethrough, which method comprises exposing said condyle, locating the condyle in a position of flexion with its posterior portion immediately adjacent the tibia, forming in the inferior portion of the condyle a bore which is axially parallel to the longitudinal axis of the femur and located radially at a first predetermined spacing from the tibia in said position of flexion, forming a condyle to a shape substantially complementary to said surface of revolution, and locating said complementary shape coaxially with said bore and at a second predetermined spacing from the tibia in a position of full extension for said condyle.

2. A method according to claim 1 wherein said first predetermined spacing and second predetermined spacing are substantially equal.

3. A prosthetic femoral component for the knee joint, comprising:

a body having a bearing surface and a bone engaging surface in back-to-back disposition;

said bearing surface being of three-dimensionally curved convex shape to serve a condylar articulation function;

said bone engaging surface being concave configured for fixation to the bone of a femur; and said bone engaging surface having a major concave segment curved in each of three-dimensions thereby substantially defining a surface of revolution about an axis therethrough, and a substantially planar minor segment extending parallel to said axis.

4. A component according to claim 3, wherein said body is elongated and has first and second opposite, mutually adjoining end portions and said major and minor segments each extending over a respective end portion of said elongated body.

5. A component according to claim 1 wherein at least one of said bearing surface and said major segment is spherically shaped.

6. A component according to claim 5 wherein both of said bearing surface and said major area are spherically shaped in mutually concentric manner.

7. A component according to claim 3 wherein said body has an elongated member projecting from said major segment along said axis.

8. A component according to claim 7 wherein said member is generally cylindrical, having a substantially circular cross-section.

9. A component according to claim 7 wherein said member projects from said major segment a distance within the perimeter of said body.

10. A prosthetic femoral component for the knee joint, comprising:

a elongated body having a bearing surface and a bone engaging surface in back-to-back disposition and having first and second opposite, mutually adjoining end portions;

said bearing surface being of convex spherical shape to serve a condylar articulation function;

said bone engaging surface being concave configured for fixation to the bone of a femoral condyle, and having major and minor segments extending over a respective end portion of said elongated body;

said major segment being curved in each of three dimensions so as to be of concave substantially spherical shape concentric with said convex spherical shape;

said minor segment being of substantially plane shape extending as a chord of said convex spherical shape; and said major segment having an elongated member projecting therefrom along a common radius of said convex and concave spherical shapes parallel with said minor segment.

* * * * *